United States Patent
Donato et al.

(10) Patent No.: US 12,337,088 B2
(45) Date of Patent: Jun. 24, 2025

(54) DIFFUSION DEVICE

(71) Applicant: GAMBRO LUNDIA AB, Lund (SE)

(72) Inventors: Danilo Donato, Cosenza (IT); Michael Kolb, Starzach (DE)

(73) Assignee: GAMBRO LUNDIA AB, Lund (SE)

( * ) Notice: Subject to any disclaimer, the term of this patent is extended or adjusted under 35 U.S.C. 154(b) by 833 days.

(21) Appl. No.: 17/415,288

(22) PCT Filed: Dec. 20, 2019

(86) PCT No.: PCT/EP2019/086512
§ 371 (c)(1),
(2) Date: Jun. 17, 2021

(87) PCT Pub. No.: WO2020/127865
PCT Pub. Date: Jun. 25, 2020

(65) Prior Publication Data
US 2022/0054722 A1    Feb. 24, 2022

(30) Foreign Application Priority Data
Dec. 21, 2018 (EP) .................... 18215661

(51) Int. Cl.
*A61M 1/16* (2006.01)
*B01D 69/08* (2006.01)

(52) U.S. Cl.
CPC .......... *A61M 1/1698* (2013.01); *B01D 69/08* (2013.01); *A61M 1/1625* (2014.02); *A61M 2202/0413* (2013.01); *B01D 2313/21* (2013.01)

(58) Field of Classification Search
CPC .... A61M 1/1698; A61M 1/1625; A61M 1/16; A61M 1/3627; A61M 60/38; A61M 2205/3334; A61M 1/32; A61M 2205/3331; A61M 1/3621; A61M 2202/0413; A61M 2202/10; A61M 2202/20; B01D 2313/21; B01D 2313/08; B01D 2313/105; B01D 63/02; B01D 2313/205; B01D 2313/201; B01D 2313/20; B01D 69/08; Y10S 261/28; Y10S 128/03
USPC ...... 604/6.14; 422/48, 44, 45; 95/43, 45, 46, 95/54; 96/4, 6, 8, 10, 155; 210/150, 210/151; 261/2
See application file for complete search history.

(56) References Cited

U.S. PATENT DOCUMENTS

| 4,642,089 A | * | 2/1987 | Zupkas | A61M 1/3632 |
| | | | | 210/438 |
| 5,240,677 A | * | 8/1993 | Jones | A61M 1/1625 |
| | | | | 210/321.74 |
| 5,263,982 A | * | 11/1993 | Shimomura | B01D 63/04 |
| | | | | 623/23.65 |

(Continued)

FOREIGN PATENT DOCUMENTS

| DE | 3711695 | 10/1988 |
| DE | 3711695 A1 * | 10/1988 |

OTHER PUBLICATIONS

PCT Search Report and Written Opinion prepared for PCT/EP2019/086512, completed Feb. 26, 2020.

*Primary Examiner* — Catharine L Anderson
*Assistant Examiner* — Quynh Dao Le
(74) *Attorney, Agent, or Firm* — Barnes & Thornburg LLP

(57) ABSTRACT

The present disclosure relates to a diffusion device, such as a blood oxygenator or gas exchanger, having improved flow characteristics.

20 Claims, 4 Drawing Sheets

(56) References Cited

U.S. PATENT DOCUMENTS

| | | | | |
|---|---|---|---|---|
| 5,266,265 A * | 11/1993 | Raible | ............... | A61M 60/849 |
| | | | | 422/46 |
| 5,304,312 A * | 4/1994 | Forster | ............... | B01D 29/96 |
| | | | | 210/321.74 |
| 5,676,526 A * | 10/1997 | Kuwana | ............... | A61M 60/113 |
| | | | | 417/423.1 |
| 5,817,279 A * | 10/1998 | Eilers | ............... | B01D 63/04 |
| | | | | 422/46 |
| 7,871,566 B2 | 1/2011 | Strauss et al. | | |
| 8,647,569 B1 | 2/2014 | Federspiel et al. | | |
| 2013/0168307 A1* | 7/2013 | Drivarbekk | ............ | B01D 61/18 |
| | | | | 210/321.78 |
| 2013/0209314 A1* | 8/2013 | Roller | ............... | A61M 1/36 |
| | | | | 422/46 |
| 2015/0165106 A1* | 6/2015 | Buck | ............... | B01D 61/28 |
| | | | | 210/321.8 |
| 2018/0078695 A1* | 3/2018 | Plott | ............... | B01D 61/28 |

* cited by examiner

DIFFUSION DEVICE

CROSS-REFERENCE TO RELATED APPLICATIONS

This application is a national stage entry under 35 U.S.C. § 371(b) of PCT International Application No. PCT/EP2019/086512, filed Dec. 20, 2019, which claims the benefit of European Patent Application Serial No. 18215661.2, filed on Dec. 21, 2018, the entire disclosures of both of which are incorporated herein by reference.

TECHNICAL FIELD

The present disclosure relates to a diffusion device, such as a blood oxygenator or gas exchanger, having improved flow characteristics.

DESCRIPTION OF THE RELATED ART

Diffusion devices used as blood oxygenators or gas exchangers generally encompass a tubular casing with a bundle of hollow fiber membranes arranged in the casing in a way that a seal is provided between the first flow space formed by the fiber cavities and a second flow space surrounding the membranes on the outside. One problem with the design of the blood inflow connected to the second flow space is to distribute the liquid evenly between the individual fibers of the hollow fiber bundle, and to avoid the formation of dead zones in the inlet, i.e. areas where the flow velocity is about zero. Blood clots may form in such dead zones, and after completion of a treatment, some of the patient's blood remains there. As the diameter of the inlet is smaller than the diameter of the fiber bundle, the velocity of the blood-flow is reduced. The design of the inlet therefore is of particular importance to ensure optimal operation of the device.

DE 37 11 695 A1 discloses a distribution cap with a rotationally symmetrical flow channel of diffusor-like design for a device for the extracorporeal treatment of blood or its components, it being possible for a core whose length is smaller than the length of the flow channel to be provided toward the end of the flow channel. The contour of the flow channel and of the core is fixed by one equation, and this results in guidance of the flow in the flow channel in such a way that there is no flow separation or dead water areas, a linear delay of the flow rate over the entire length of the flow channel and hence a quadratic decrease in the averaged flow rate being achieved.

U.S. Pat. No. 7,871,566 B2 teaches a device for enriching and/or depleting substances in a liquid. The device comprises a membrane module that consists essentially of concentric elements and that has a separation element in which the substance to be enriched and/or depleted is carried, and whereby the liquid is carried outside of the separation element; a drive module that encompasses a drive unit for driving a conveying element that conveys the liquid, the drive unit having a radial magnetic coupling for a central impeller located on the inside; a conveying module for conveying the liquid through the device, housing the conveying element, whereby the drive module is adapted to be inserted into and removed from the membrane module with a liquid-tight closure; an oxygenator having an outside fiber bundle and an inside fiber bundle; and an electromagnetic drive unit disposed between the outside fiber bundle and the inside fiber bundle.

U.S. Pat. No. 8,647,569 B1 discloses a veno-venous extracorporeal oxygenator with an annular cylindrical hollow fiber membrane bundle that is rotated at rapidly varying speeds. Blood is introduced to the center of the device and is passed radially through the fiber bundle. The bundle is rotated at rapidly changing velocities with a rotational actuator. The rotation of the fiber bundle provides centrifugal kinetic energy to the blood giving the device pumping capabilities and may create Taylor vortexes to increase mass transfer. Rotation of the fiber bundle increases the relative velocity between the blood and the hollow fibers and increases the mass transfer.

SUMMARY

It is an object of the present invention to provide a diffusion device with a more homogeneous blood flow within the device and no areas where the blood velocity is nearly zero (dead zones).

According to one aspect of the invention, a diffusion device having improved flow characteristics is provided. The device comprises a cylindrical housing, a plurality of hollow fiber membranes arranged within the housing, and end caps sealing the mouths of the housing.

DETAILED DESCRIPTION

Figure 1:
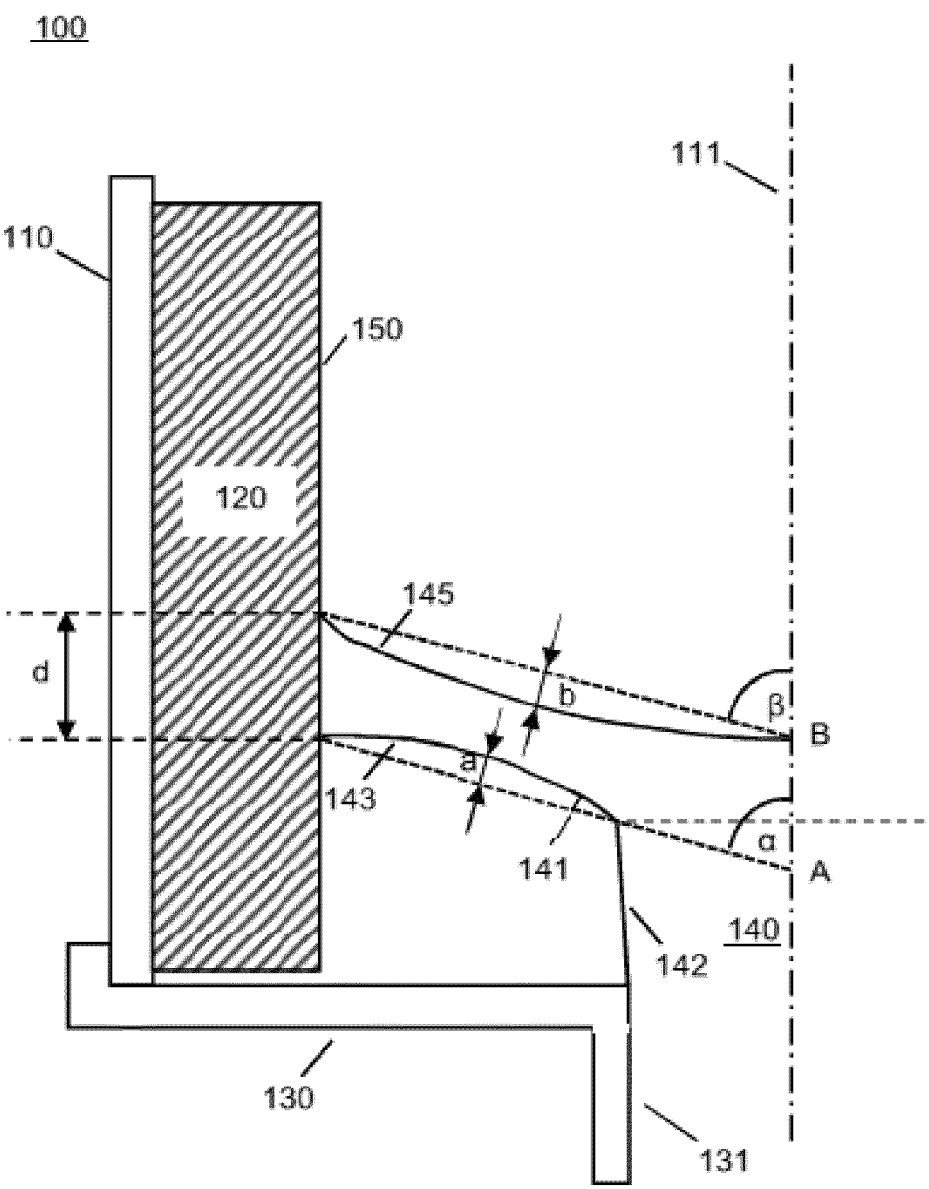
FIG. 1 shows a schematic partial cross-sectional view of an embodiment of the diffusion device of the present disclosure.

The diffusion device of the present disclosure comprises a cylindrical housing. In one embodiment, the cylindrical housing provides an outlet for blood arranged on the outer wall of the housing. In a further embodiment, the blood outlet is located near an end of the cylindrical housing opposite to a first end cap. In one embodiment, the cylindrical housing is comprised of polycarbonate.

A plurality of semi-permeable hollow fiber membranes is disposed inside the housing within a cylindrical shell adjoining the inner wall of the housing.

In one embodiment, the semi-permeable hollow fiber membranes are gas exchange membranes, i.e., they are permeable to gases like oxygen and carbon dioxide, but impermeable to liquids.

In a further embodiment, the semi-permeable hollow fiber membranes are arranged in the form of hollow fiber mats wound on a cylindrical core. The hollow fiber mats form a cylindrical shell that contacts the inner surface of the cylindrical housing. The ends of the hollow fibers are open, so that a gas flow can be conducted through the lumen of the hollow fibers, i.e., from one mouth of the housing to the mouth opposite to it. During operation of the diffusion device, blood flows on the outside of the hollow fibers, and gas can permeate through the wall of the hollow fibers in both directions. In one embodiment of the device, the flow space formed by the lumen of the hollow fibers is separated from the flow space on the outside of the hollow fibers by end walls. In one embodiment, the end walls are formed by potting the fiber ends with a polyurethane resin. After the resin has hardened, the ends of the hollow fibers are cut off to re-open the lumen of the hollow fibers.

The diffusion device comprises a first end cap sealing a first mouth of the housing. The end cap comprises an inlet for the introduction of blood into the housing, arranged axially in the center of the first end cap. In one embodiment, a two-start thread which fits a standard blood-line connector is provided round the inlet. The inner surface of the end cap is rotationally symmetrical about the longitudinal axis of the inlet. The inlet is also coaxial to the longitudinal axis of the housing. In a further embodiment, the end cap also comprises an outlet for evacuating a gas from the diffusion device, e.g., a gas mixture comprising carbon dioxide.

The diffusion device comprises a rotationally symmetric blood duct connecting the inlet to an inner perimeter of the cylindrical shell. The blood duct is defined by a first inner surface and a second inner surface.

The first inner surface comprises, in the direction of increasing diameter, a first section taking the form of a cylinder or a truncated cone, and a second section connecting the first section and the inner perimeter of the cylindrical shell. The second section takes the form of a torus segment, with an angle a between the longitudinal axis of the cylindrical housing and a straight line (A) intersecting i) the longitudinal axis, ii) the intersection of the first section and the second section, and iii) the intersection of the second section and the inner perimeter of the cylindrical shell. In the diffusion device of the present disclosure, the angle α is in the range of from 55° to 80°, and the maximum of a perpendicular distance (a) between the straight line (A) and the surface of the second section is in the range of from 0.5 to 1 mm. In one embodiment of the diffusion device of the present disclosure, the angle α is in the range of from 70° to 80°. In one embodiment, the radius of curvature of 5 the second section is in the range of from 18 to 21 mm.

The second inner surface spans the inner perimeter of the cylindrical shell, i.e., the second inner surface spans the complete cross-section of the hollow cylinder confined by the cylindrical shell. In the diffusion device of the present disclosure, an angle β between the longitudinal axis of the cylindrical housing and a straight line (B) intersecting i) the longitudinal axis at its intersection with the second inner surface and ii) the intersection of the second inner surface and the inner perimeter of the cylindrical shell is in the range of from 55° to 80°, and the maximum of a perpendicular distance (b) between the straight line (B) and the surface of the second inner surface is in the range of from 0.5 to 1 mm. In one embodiment of the diffusion device of the present disclosure, the angle β is in the range of from 70° to 80°.

In the diffusion device of the present disclosure, a distance (d) between the first inner surface and the second inner surface at the inner perimeter of the cylindrical shell is in the range of from 2 to 3 mm; and a minimal distance between the second section of the first inner surface and the second inner surface is not less than 1 mm. In one embodiment of the diffusion device, the minimal distance is 1.0 mm.

In one embodiment of the diffusion device of the present disclosure, the maximum of the perpendicular distance (a) is (0.5±0.05) mm; the maximum of the perpendicular distance (b) is (0.5±0.05) mm; and the minimal distance between the second section of the first inner surface and the second inner surface is (1±0.1) mm.

In one embodiment of the diffusion device of the present disclosure, the radius of curvature of the second inner surface is smaller at the center of the second inner surface than the radius of curvature opposite the second section of the first inner surface. In one embodiment, the radius of curvature opposite the second section of the first inner surface is in the range of from 22 to 26 mm. In a further embodiment, the radius of curvature at the center of the second inner surface is in the range of from 2 to 4 mm.

In one embodiment of the diffusion device of the present disclosure, the first section of the first inner surface takes the form of a cylinder. In another embodiment, the first section of the first inner surface takes the form of a truncated cone with an aperture in the range of from 0.1° to 2°.

In one embodiment of the diffusion device of the present disclosure, the rotationally symmetric blood duct is formed by assembling a first component part having an outer surface that provides the first inner surface of the blood duct and a second component part having an outer surface that provides the second inner surface of the blood duct.

In one embodiment, the outer surface of the first component part which provides the first inner surface of the blood duct features at least three protrusions and the outer surface of the second component part which provides the second inner surface of the blood duct features corresponding depressions. The protrusions and corresponding depressions are configured to interact upon assembly of the first and second component parts and determine the spacing between the first and second inner surfaces of the blood duct. In a further embodiment, four protrusions and four corresponding depressions are equally distributed over a circumference of the parts, i.e., at 0°, 90°, 180°, and 270°.

In one embodiment, the outer surface of the first component part which provides the first inner surface of the blood duct features at least three depressions and the outer surface of the second component part which provides the second inner surface of the blood duct features corresponding protrusions. The depressions and corresponding protrusions are configured to interact upon assembly of the first and second component parts and determine the spacing between the first and second inner surfaces of the blood duct.

In one embodiment of the diffusion device of the present disclosure, the first and second component parts are comprised of polycarbonate.

An embodiment of the diffusion device of the present disclosure additionally comprises a second end cap sealing a second mouth of the housing, i.e. the mouth opposite the mouth with the first end cap. The second end cap provides an inlet for introducing a gas, e.g., air or oxygen, into the diffusion device.

The housing and end caps of the device of the present disclosure are usually made of a transparent polymer, e.g., polyethylene, polypropylene, polyesters like PET or PBT, polymethyl(meth)acrylate, polystyrene (HIPS), or polycarbonate. The potting material for the hollow fiber membranes usually is polyurethane. In one embodiment of the device of the invention, the housing and caps are made of polycarbonate, the potting material forming the end walls is comprised of polyurethane.

The diffusion device of the present disclosure will now be described in more detail referring to the accompanying drawings. It is to be understood that the drawings are not intended to limit the scope of the present disclosure and are merely an illustration of preferred embodiments of the device.

FIG. 1 shows a partial cross-sectional view of an embodiment of the diffusion device 100 proposed in the present disclosure. As the device 100 is rotationally symmetrical to the longitudinal axis 111 of the device 100, only one half of the cross-section is shown in FIG. 1. As shown in FIG. 1, the device 100 comprises an inlet 131 for blood, arranged axially in the center of a first end cap 130 of the device 100. The inner surface of the end cap 130 is rotationally symmetrical about the longitudinal axis of the inlet, which is also the longitudinal axis of the end cap 130 and the longitudinal axis 111 of the housing 110. The inlet 131 is coaxial to the longitudinal axis 111 of the housing 110.

A plurality of semi-permeable hollow fiber membranes 120 is disposed inside the housing 110 within a cylindrical shell adjoining the inner wall of the housing 110. An inner perimeter 150 of the cylindrical shell defines a cavity within the housing 110.

A rotationally symmetric blood duct 140 connects the inlet 131 to the inner perimeter 150 of the cylindrical shell. The blood duct 140 is defined by a first inner surface 141 and a second inner surface 145.

The first inner surface 141 comprises, in the direction of increasing diameter, a first section 142 having the form of a truncated cone, and a second section 143 connecting the first section 142 and the inner perimeter 150 of the cylindrical shell. The second section 143 has the form of a torus segment. An angle α between the longitudinal axis 111 of the cylindrical housing 110 and a straight line A intersecting i) the longitudinal axis 111, ii) the intersection of the first section 142, and the second section 143, and iii) the intersection of the second section 143 and the inner perimeter 150 of the cylindrical shell is in the range of from 55° to 80°. The maximum of a perpendicular distance a between the straight line A and the surface of the second section 143 is in the range of from 0.5 to 1 mm.

The second inner surface 145 spans the inner perimeter 150 of the cylindrical shell. An angle β between the longitudinal axis 111 of the cylindrical housing 110 and a straight line B intersecting i) the longitudinal axis 111 at its intersection with the second inner surface 145 and 25 ii) the intersection of the second inner surface 145 and the inner perimeter 150 of the cylindrical shell is in the range of from 55° to 80°. The maximum of a perpendicular distance b between the straight line B and the surface of the second inner surface 145 is in the range of from 0.5 to 1 mm.

A distance d between the first inner surface 141 and the second inner surface 145 at the inner perimeter 150 of the cylindrical shell is in the range of from 2 to 3 mm. A minimal distance between the second section 143 of the first inner surface 141 and the second inner surface 145 is not less than 1 mm.

Figure 2:
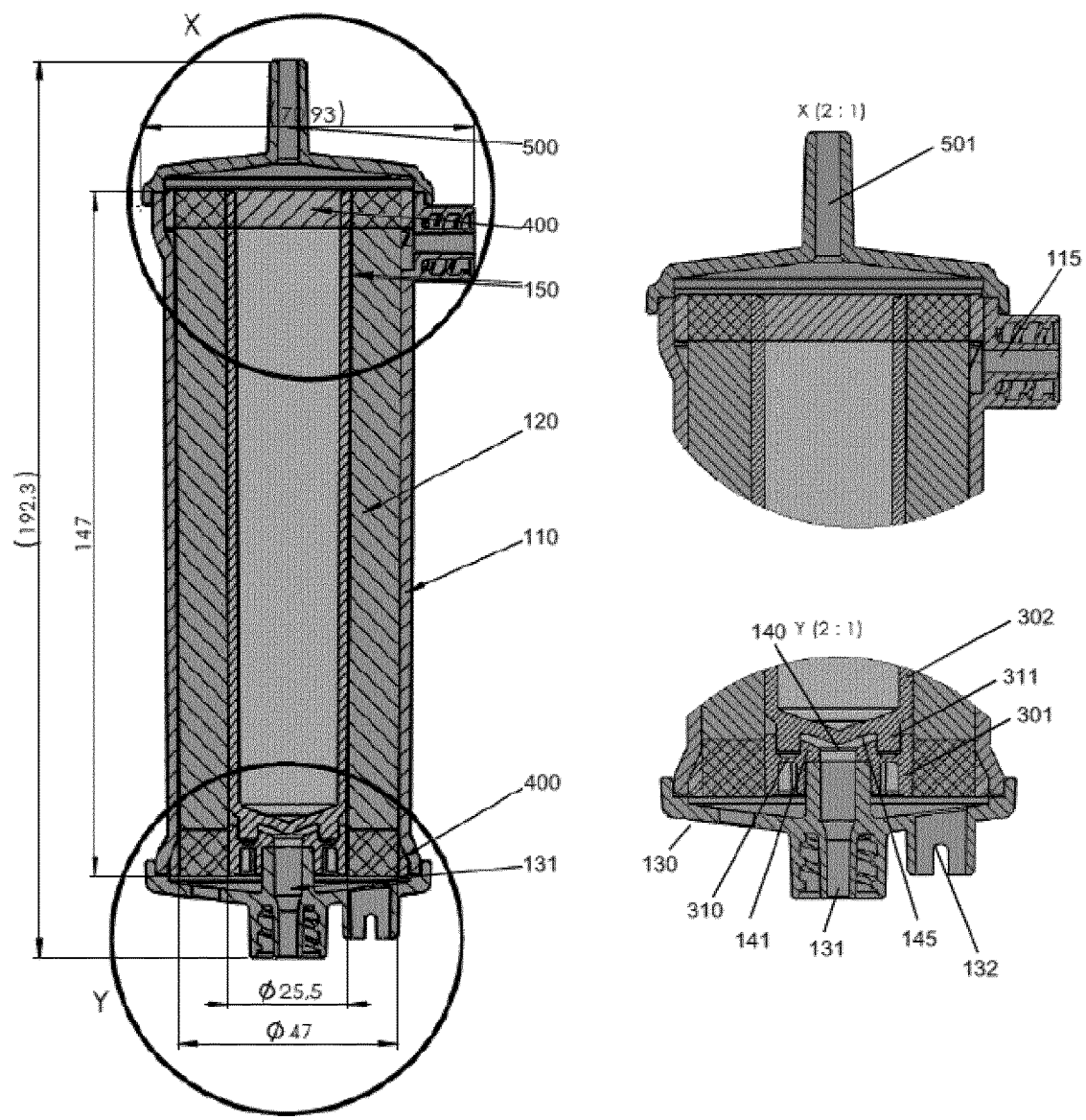
FIG. 2 shows a side, cross-sectional view of another embodiment of the of the diffusion device of the present disclosure.

FIG. 2 shows a cross-sectional view of another embodiment of the diffusion device 100 of the present disclosure. Enlarged detail views X and Y of the device are also shown. The mouths of cylindrical housing 110 are covered by a first end cap 130 and a second end cap 500, respectively. The housing 110 has a blood inlet 115 positioned on the outer wall of the hosing adjacent to the second end cap 500. The first end cap 130 features a blood inlet 131 and a gas outlet 132, the second end cap 500 a gas inlet 501. Hollow fibers 120 are arranged within the housing 110 within a cylindrical shell bordering on the inner wall surface of the housing 110 and limited by perimeter 150. End walls 400 separate a first flow space formed by the lumen of the hollow fibers 120 and cavities defined by the second end cap 500 and the first end cap 130 from a second flow space defined by blood inlet 131, blood duct 140, and the space outside the hollow fibers 120 within the circular shell, i.e., between the inner wall surface of the housing 110 and the perimeter 150. A core formed by an assembly of two component parts 301 and 302 is arranged in the cavity limited by perimeter 150. Component part 301 features four depressions 310, component part 302 has four corresponding protrusions 311. The protrusions 311 enter the depressions 310 upon assembly of the core and together form blood duct 140, component part 301 defining a first surface 141; and component part 302 defining a second surface 145 of the blood duct 140.

Figure 3:
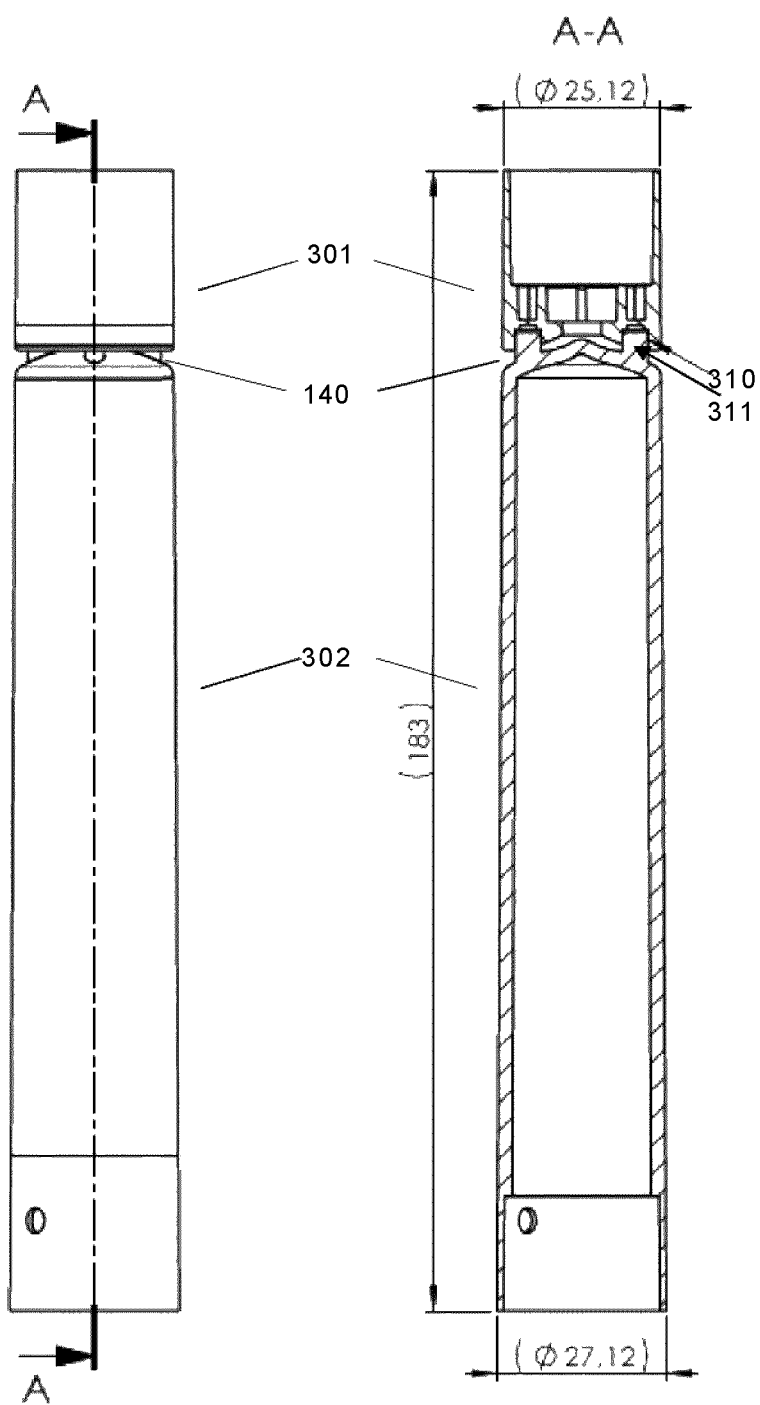
FIG. 3 shows a side view and a cross-sectional view of an assembly of two component parts providing the blood duct of an embodiment of the diffusion device of the present disclosure.

FIG. 3 shows a side view and a cross-sectional view of an assembly of two component parts 301 and 302 providing the blood duct 140 of an embodiment of the diffusion device of the present disclosure. Component part 301 features four depressions 310, component part 302 has four corresponding protrusions 311. The protrusions 311 enter the depressions 310 upon assembly of the core and together form blood duct 140.

Figure 4:
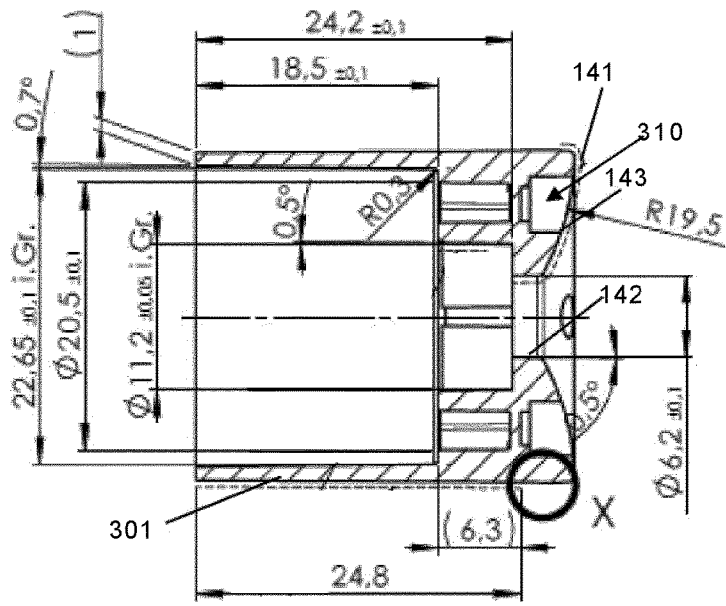
FIG. 4 shows a cross-sectional view of a first component part for providing the blood duct of an embodiment of the diffusion device of the present disclosure.

FIG. 4 shows a cross-sectional view of a first component part 301 for providing the blood duct of an embodiment of the diffusion device of the present disclosure. An outer surface 141 of component part 301 provides a first surface of the blood duct. The surface 141 has a first section 142 and a second section 143. In the embodiment shown, the first section 142 has the form of a frustrated cone having an aperture of 1°; and the second section 143 has the form of a torus segment with a radius of curvature of 19.5 mm. Component part 301 features four depressions 310 that are configured to interact with corresponding protrusions of a second component part.

Figure 5:
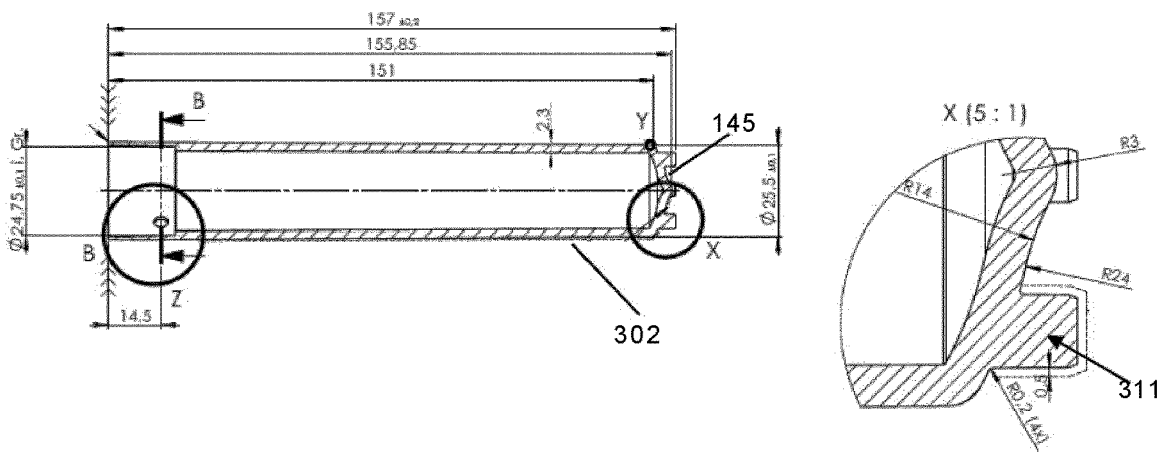
FIG. 5 shows a cross-sectional view of a second component part for providing the blood duct of an embodiment of the diffusion device of the present disclosure.

FIG. 5 shows a cross-sectional view of a second component part 302 for providing the blood duct of an embodiment of the diffusion device of the present disclosure and an enlarged detail view X of component part 302. An outer surface 145 of component part 302 provides a second surface of the blood duct. In the embodiment shown, the surface 145 has a smaller radius of curvature at its center than at its perimeter. The radius of curvature at the center of surface 145 is 3 mm, while the radius of curvature of the surface 145 further away from its center is 24 mm. Component part 302 features four protrusions 311 that are configured to interact with corresponding protrusions of a second component part.

LIST OF REFERENCE SIGNS 100 diffusion device
110 cylindrical housing
111 longitudinal axis of cylindrical housing
115 blood outlet
120 hollow fiber membranes/cylindrical shell
130 first end cap
131 blood inlet
132 air outlet
140 blood duct
141 first inner surface
142 first section of first inner surface
143 second section of first inner surface
145 second inner surface
150 inner perimeter of cylindrical shell
301 first component part
302 second component part
310 depression
311 protrusion 400 end wall
500 second end cap
501 air inlet

The invention claimed is:
1. A diffusion device comprising
   a) a cylindrical housing;
   b) a plurality of semi-permeable hollow fiber membranes disposed within a cylindrical shell inside the cylindrical housing, wherein the cylindrical shell is formed by the hollow fiber membranes and contacts an inner wall of the cylindrical housing;
   c) a first end cap sealing a first mouth of the cylindrical housing and comprising an inlet for introduction of blood into the cylindrical housing, the inlet being coaxial to a longitudinal axis of the cylindrical housing; and
   d) a rotationally symmetric blood duct connecting the inlet to an inner perimeter of the cylindrical shell, the blood duct being defined by a first inner surface and a second inner surface,
   the first inner surface comprising, in a direction of increasing diameter, a first section taking a form of a cylinder or a truncated cone, and a second section connecting the first section and the inner perimeter of the cylindrical shell, the second section taking a form of a torus segment, with an angle between the longitudinal axis of the cylindrical housing and a straight line (A) intersecting i) the longitudinal axis, ii) an intersection of the first section and the second section, and iii) an intersection of the second section and the inner perimeter of the cylindrical shell being in a range from 55° to 80°, and a maximum of a perpendicular distance (a) between the straight line (A) and a surface of the second section being in a range from 0.5 to 1 mm;
   the second inner surface spanning the inner perimeter of the cylindrical shell, with an angle (b) between the longitudinal axis of the cylindrical housing and a straight line (B) intersecting i) the longitudinal axis at its intersection with the second inner surface and ii) an intersection of the second inner surface and the inner perimeter of the cylindrical shell being in a range from 55° to 80°, and a maximum of a perpendicular distance (b) between the straight line (B) and the surface of the second inner surface being in a range from 0.5 to 1 mm;
   a distance (d) between the first inner surface and the second inner surface at the inner perimeter of the cylindrical shell being in a range from 2 to 3 mm; and a minimal distance between the second section of the first inner surface and the second inner surface being not less than 1 mm, wherein a maximum distance between a center of the second inner surface and a center of the second section of the first inner surface is less than the distance (d).

2. The diffusion device of claim 1, wherein the maximum of the perpendicular distance (a) is (0.5+0.05) mm; the maximum of the perpendicular distance (b) is (0.5+0.05) mm; and the minimal distance between the second section of the first inner surface and the second inner surface is (1+0.1) mm.

3. The diffusion device of claim 2, wherein the radius of curvature of the second inner surface at the center of the second inner surface is smaller than the radius of curvature opposite the second section of the first inner surface.

4. The diffusion device of claim 2, wherein the first section of the first inner surface takes the form of a truncated cone with an aperture in the range from 0.1° to 2°.

5. The diffusion device of claim 2, wherein the rotationally symmetric blood duct is formed by assembling a first component part having an outer surface that provides the first inner surface of the blood duct and a second component part having an outer surface that provides the second inner surface of the blood duct.

6. The diffusion device of claim 5, wherein the outer surface of the first component part which provides the first inner surface of the blood duct features at least three protrusions and the outer surface of the second component part which provides the second inner surface of the blood duct features corresponding depressions; and the protrusions and corresponding depressions are configured to interact upon assembly of the first and second component parts and determine the spacing between the first and second inner surfaces of the blood duct.

7. The diffusion device of claim 5, wherein the outer surface of the first component part which provides the first inner surface of the blood duct features at least three depressions and the outer surface of the second component part which provides the second inner surface of the blood duct features corresponding protrusions; and the depressions and corresponding protrusions are configured to interact upon assembly of the first and second component parts and determine the spacing between the first and second inner surfaces of the blood duct.

8. The diffusion device of claim 5, wherein the first and second component parts are comprised of polycarbonate.

9. The diffusion device of claim 2 additionally comprising a second end cap sealing a second mouth of the cylindrical housing.

10. The diffusion device of claim 1, wherein a radius of curvature of the second inner surface at the center of the second inner surface is smaller than a radius of curvature opposite the second section of the first inner surface.

11. The diffusion device of claim 10, wherein the first section of the first inner surface takes the form of a truncated cone with an aperture in the range from 0.1° to 2°.

12. The diffusion device of claim 10 additionally comprising a second end cap sealing a second mouth of the cylindrical housing.

13. The diffusion device of claim 1, wherein the first section of the first inner surface takes the form of a truncated cone with an aperture in a range from 0.1° to 2°.

14. The diffusion device of claim 13 additionally comprising a second end cap sealing a second mouth of the cylindrical housing.

15. The diffusion device of claim 1, wherein the rotationally symmetric blood duct is formed by assembling a first component part having an outer surface that provides the first inner surface of the blood duct and a second component part having an outer surface that provides the second inner surface of the blood duct.

16. The diffusion device of claim 15, wherein the outer surface of the first component part which provides the first inner surface of the blood duct features at least three protrusions and the outer surface of the second component part which provides the second inner surface of the blood duct features corresponding depressions; and the protrusions and corresponding depressions are configured to interact upon assembly of the first and second component parts and determine the spacing between the first and second inner surfaces of the blood duct.

17. The diffusion device of claim 15, wherein the outer surface of the first component part which provides the first inner surface of the blood duct features at least three depressions and the outer surface of the second component part which provides the second inner surface of the blood duct features corresponding protrusions; and the depressions and corresponding protrusions are configured to interact upon assembly of the first and second component parts and determine the spacing between the first and second inner surfaces of the blood duct.

18. The diffusion device of claim 15, wherein the first and second component parts are comprised of polycarbonate.

19. The diffusion device of claim 1, additionally comprising a second end cap sealing a second mouth of the cylindrical housing.

20. The diffusion device of claim 1, wherein the semi-permeable hollow fiber membranes are impermeable to liquids and permeable to gases.

* * * * *